(12) United States Patent
Stancioiu et al.

(10) Patent No.: US 10,543,242 B2
(45) Date of Patent: Jan. 28, 2020

(54) COMPOSITION FOR THE TREATMENT OF JOINT CONDITIONS

(71) Applicants: Felician Stancioiu, Bucharest (RO); Daniele Catanas, Bucharest (RO)

(72) Inventors: Felician Stancioiu, Bucharest (RO); Daniele Catanas, Bucharest (RO)

(*) Notice: Subject to any disclaimer, the term of this patent is extended or adjusted under 35 U.S.C. 154(b) by 584 days.

(21) Appl. No.: 14/967,200

(22) Filed: Dec. 11, 2015

(65) Prior Publication Data

US 2016/0095890 A1   Apr. 7, 2016

Related U.S. Application Data

(60) Provisional application No. 62/090,401, filed on Dec. 11, 2014.

(51) Int. Cl.

| | | |
|---|---|---|
| *A61K 36/28* | (2006.01) | |
| *A61K 36/752* | (2006.01) | |
| *A61K 36/899* | (2006.01) | |
| *A61K 36/30* | (2006.01) | |
| *A61K 45/06* | (2006.01) | |
| *A61K 9/107* | (2006.01) | |
| *A61K 9/06* | (2006.01) | |

(52) U.S. Cl.
CPC .............. *A61K 36/28* (2013.01); *A61K 36/30* (2013.01); *A61K 36/752* (2013.01); *A61K 36/899* (2013.01); *A61K 45/06* (2013.01); *A61K 9/06* (2013.01); *A61K 9/107* (2013.01)

(58) Field of Classification Search
None
See application file for complete search history.

(56) References Cited

U.S. PATENT DOCUMENTS

| | | | | |
|---|---|---|---|---|
| 6,977,081 | B1 * | 12/2005 | Rood | A61K 8/23 424/400 |
| 7,195,781 | B2 * | 3/2007 | Miketin | A61K 36/185 424/520 |
| 8,178,106 | B2 * | 5/2012 | Hines | A61K 8/97 424/195.16 |

FOREIGN PATENT DOCUMENTS

JP   2005002057 A * 1/2005
WO   WO 2013/162135 A1 * 10/2013

* cited by examiner

*Primary Examiner* — Susan Hoffman
(74) *Attorney, Agent, or Firm* — Michael D. Eisenberg

(57) ABSTRACT

The present invention relates to a composition for improving the health status of various joints in the human body. The composition includes at least one plant extract as fatty base with active role, at least one extract from plants with anti-microbial properties, at least one extract from plants with analgesic and/or anti-inflammatory properties, and at least one extract from plants with anti-rheumatic and regenerative properties, to which dimethylsulfoxide, allantoin and/or potassium alum may be added. The composition may be used to treat osteoarthritis, rheumatic joint disease, joint swelling, pain, hallux valgus, traumatic conditions of the joints including sprains, strains, post-surgical recovery, bone edema, and speed up the recovery of athletes post-injury.

4 Claims, No Drawings

COMPOSITION FOR THE TREATMENT OF JOINT CONDITIONS

CROSS-REFERENCES TO RELATED APPLICATIONS

This application claims priority from U.S. Provisional Application Ser. No. 62/090,401 filed Dec. 11, 2014, which is hereby incorporated herein by reference in the respective in its entirety.

TECHNICAL FIELD

The present invention, in some embodiments thereof, relates to health and natural products. Specifically it relates to products to improve the structure and function of diseased articulations (joints) of the body by alleviating articular (joint) pain, inflammation and swelling.

BACKGROUND OF THE INVENTION

Joint pain, swelling and deformity are relatively common complaints in elderly patients. These symptoms are usually caused by the deterioration of the joint cartilage that occurs with age, and/or by conditions associated with inflammation, trauma or reduced synovial liquid in the joints. Pain is frequently severe and requires administration of drugs with anti-inflammatory properties but which also have important adverse effects (gastritis, cardiovascular events, etc.) that occur especially with the extended use needed to treat these chronic articular ailments. Such drugs may include analgesics (painkillers) (such as acetaminophens and modified opioids), and NSAIDs (non-steroidal anti-inflammatory drugs), such as COX-1 and COX-2 inhibitors (e.g., Alevia, Celebrex, etc.). Other treatments used for alleviating the pain include steroids which may be delivered orally or intra-articularly (e.g. Prednisone, Hyalgan, Synvisc, etc), monoclonal antibodies which block molecules associated with the inflammatory response (e.g., Enbrel), and surgery (both classic and endoscopic) to extricate damaged cartilage and in severe cases to replace the affected joint.

Utilization of drugs in the form of topical ointments mitigates the adverse effects, but is usually regarded as less effective due to limited availability of the active substance in the affected tissue. While topical ointments may have reduced adverse effects, they still present the same drug safety profiles (they cause similar adverse effects).

The drugs and treatments used for decreasing pain may cause adverse side effects of different severity and health manifestations: some obvious (gastritis, gastro-esophageal reflux, gastric ulcer, etc.) and some more insidious (cardiovascular deterioration with increased risk for cardiovascular events).

Natural extracts from various plants have been used traditionally. Plant extracts are generally regarded as having less side effects but also as being less effective than drugs.

Commonly used extracts used with some success and mostly as individual extracts for relieving pain and symptoms associated with degenerative joint diseases include extracts of Juniperus, Helleborus, Tamus, Salix, Pinus. These extracts are mixed with a base made of mineral fats (e.g., paraffin) or other fatty substances with non-vegetal origin (lanolin, beeswax), or animal fat. In order to maintain high miscibility of the plant extracts with the base, emulsifiers, correctors, and preservatives are used.

The miscibility of plant extracts with mineral fats or non-vegetal fatty substances is low. Thus, emulsifiers are required in such mixtures, to keep the plant extracts evenly dispersed in the base. Adding an emulsifier or preservative as a specialized substance increases the possibility of allergic and other adverse reactions (one such example is the recent banning of parabens use in Europe), and increases the number of ingredients and manufacturing costs without adding therapeutic benefits.

The plant (vegetal) fats contains ample amounts of fatty acids which have been by themselves used successfully to treat arthritis and joint pain; one such example is a mixture of mainly long-chained, saturated fatty acids (stearic, linoleic, myristic, etc.) which are available to be administered both systemically (tablets) or topically (cream). However the former form increases the risk for developing insulin resistance, prediabetes and diabetes, while the latter is not as efficacious because of the low bioavailability (crossing of skin). Our composition overcomes this problem and adds to the benefits of fatty acids for treating articular problems.

Moreover, the composition bases used in the prior art have a substantial hydric content. Such bases need additional types and amounts of preservatives, mineral fats or non-vegetal to keep the plant extracts evenly dispersed in the base.

For example, a composition made in the Russian Federation for veterinarian use includes a specific, patented mix of plant extracts (*Eucalyptus, Cedrus brevifolia, Pinus sibirica, Syzygium aromaticum, Lavandula angustifolia, Rosmarinus officinalis, Potentilla erecta, Juniperus communis, Myrtus communis, Vaccinium oxycoccos, Aesculus hippocastanum, Inula helenium*, camphor, menthol cayenne, turpentine), along with dimethylsulfoxide, glycerin, methylchloroisothiasolinone, methylisothiasolinone. However the base of this prior art composition is a synthetic hidrophylic substance (polidone and carbopole in water, which together with chitosan make up more than 70% of the ointment by mass.

BRIEF SUMMARY OF EMBODIMENTS OF THE INVENTION

There is therefore a need for a composition, which effectively treats joint pain, swelling, and deformity while having decreased side effects. It would be advantageous that the composition includes plant extracts, and that the use of non-natural components be decreased.

The present invention relates to a composition, which improves the efficacy of natural extracts, while keeping their excellent safety profile.

The composition of the present invention includes just one manufactured organic compound (dimethyl sulfoxide) which is safely used currently in medicine for organ and cell transplantation and treatment of chronic interstitial cystitis.

The inventors have used the composition of the present invention to treat various pathologies of the joints, and have achieved excellent results.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

An aspect of some embodiments of the present invention relates to health and natural products. Specifically it relates to a composition for treating various conditions of the joints, and improving the functional status of various joints (ankle, knee, shoulder, elbow, wrist, fingers, lumbar and cervical spine, costochondral). The composition includes a base and optionally additional active ingredients, the latter being one or more plant extracts. The base includes a fatty substance extracted from one or more plants, dimethyl sulfoxide (DMSO), and optionally at least one of allantoin, potassium alum, and potassium chloride. The base of this composition is not inert, but acts synergistically with the chosen plant extracts and thus the composition has greatly enhanced anti-inflammatory, analgesic, anti-rheumatic, antimicrobial, calming, anti-edematous, etc. In some embodiments of the present invention, the fatty substance of the composition base forms up to 70% of the composition, the base forms up to 90% of the composition, and the plant extracts form up to 10% of the composition. Each constituent plant extract, described below, contains different active ingredients in different quantities.

The fact that the base includes only plant fats (which are also referred to as "vegetal fats") and dimethyl sulfoxide is novel and has multiple advantages. The plant fats which form most of the composition are not just an inert matrix, as in known ointments and preparations, but presents in themselves benefits towards the treatment of joint pain, swelling, and/or deformities. Thus, in some embodiments of the present invention, the base which includes fatty plant extracts and DMSO forms the whole composition. In other embodiments, plant extracts and DMSO comprise more than 95% of the composition by weight, while the rest includes two natural substances: allantoin, which is also present in significant amounts in plants, and potassium alum or potassium chloride.

Small quantities of potassium alum or potassium chloride can modify cellular membrane potentials, and may bring about beneficial analgesic effects, such as inhibition of the local peripheral nerve conduction, and probably inhibition of the activity of various receptors involved in the transmission of the discomfort and pain associated with joint damage. Potassium alum also has antiseptic properties. The inventor has found that the addition of small amounts of potassium alum and/or potassium chloride to the composition of the present invention is beneficial to patients with some conditions such as lumbago and spondylitis.

The composition does not need emulsifiers or preservatives. This is because dimethyl sulfoxide is a polar aprotic solvent that dissolves both polar and nonpolar compounds and is miscible in a wide range of organic solvents as well as water. Moreover, dimethyl sulfoxide enhances the absorption of the active ingredients of the composition through the skin and the joint capsule. Dimethyl sulfoxide itself has recognized anti-inflammatory and antioxidant properties which makes it beneficial for treating the pathological processes which occur in an inflamed, deteriorating joint. The use of a fatty plant base with negligible hydric content greatly reduces the need for antimicrobial substances and allows the natural antiseptics of the plant extracts to prevent contamination with—and development of—detrimental microorganisms.

In some embodiments of the present invention, the base includes one or more of the following fatty plant extracts: palm oil, palm kernel oil (*Elaeis guineensis*), coconut oil (*Cocos nucifera*), cocoa butter (*Theobroma cacao*), shea butter (*Vitellaria paradoxa*), mango (*Mangifera indica*), and other sources of fat from plants including hydrogenated vegetal oils or beeswax. These vegetal fats contain significant quantities of carotenoids, tocopherols, tocotrienols, sterols, phospholipids, squalene, and triterpenic and aliphatic hydrocarbons, which improve the properties of the cellular membranes, act as antioxidants, and decrease inflammation.

Optionally, the dimethyl sulfoxide is of high purity (more than 99.9% pure) and in liquid form at room temperature. Allantoin, potassium alum and potassium chloride, if present, may be in the form of solid white crystalline substances at room temperature.

The active ingredients include at least one plant extract from the each of the following groups: (a) anti-inflammatory, (b) analgesic & anti-microbial, and (c) plants with known anti-rheumatic properties (e.g. improving joint characteristics, stopping degradation of cartilage and promotion of collagen and synovial fluid formation, decreasing of inflammatory exudates and edema).

The ointment contains the following plant extracts: at least one source of fatty acids (fatty plant extract); *Erigeron canadensis, Equisetum arvense, Fraxinus excelsior, Arnica montana, Symphytum officinale*, potato (*Solanum tuberosum*); tea tree oil (*Melaleuca alternifolia*); and lemon oil (*Citrus limon*). The source of fatty acids may include, for example, one or more of: coconut oil (*Cocos nucifera*), cocoa butter (*Theobroma cacao*), beeswax, soy wax, palm oil, palm kernel oil (*Elaeis guineensis*), and shea butter (*Vitellaria paradoxa*). Optionally, the at least one source of fatty acids forms about 0.1-70% of the composition, while each of the other plant extracts forms about 0.1-5% of the composition.

In some embodiments of the present invention, the extracts with anti-inflammatory properties include extracts from the following plants: *Alangium salviflorum, Allium cepa, Allium porrum, Allium sativum, Althaea officinalis, Apium graveolens, Arctium lappa, Asparagus officinalis, Beta vulgaris, Betula pendula, Brassica nigra, Brassica oleracea sabauda, Calendula officinalis, Callisia fragrans, Centaurea cyanus, Cerasum avium, Cerasus vulgaris, Citrus* spp., *Colchium autumnale, Crocus sativus, Cucumis sativa, Cucurbita pepo, Cucurbita pepo giromontia, Cynara scolymus, Daucus carota, Echium vulgare, Erigeron Canadensis, Fragaria moschata, Fragaria vesca, Frasinus excelsior, Fumaria oficinalis, Galium aparine, Inula helenium, Juglans regia, Juniperus communis, Lactuca sativa, Lycopersicon esculentum, Malus domestica, Melilotus officinalis, Melitorus albus, Padus avium* spp., *Paeonia officinalis, Petasites hybridus, Petroselinum crispum, Phaseolus vulgaris, Physalis alkekengi, Pimpinella anisum, Plantago lanceolata, Polypodium vulgare, Populus* spp. *Primula offi-*

*cinalis, Pyrus communis, Quercus robur, Raphanus sativus niger, Raphanus sativus sativus, Ribes nigrum, Ribes rubrum, Ribes uva-crispa, Rubus idaeus, Rumex acetosa, Ruscus aesculatus, Salvia officinalis, Sambucus ebulus, Sambuccus nigra, Saponaria officinalis, Solanum tuberosum, Solidago virgaurea, Spinacea oleracea, Stellaria media, Symphytum officinale, Tamus communis, Thymus serpyllum, Urtica dioica, Urtica urens, Viola tricolor, Vitis vinifera, Zea mays, Triticum* spp, *Oryzza* spp.

In some embodiments of the present invention, the extracts with analgesic and/or microbial properties include plant extracts which include one or more of the following bio-active substances in vivo: ursolic acid, salicoside, betulene, cresol, borneol, diosphenol, isomentone, limonene, piperitone, borneol, tannin, guggusterol, terpenes, curcumin, arbutin, galic acid, diosmine, marubin, amentoflavones, desoxypodophylotoxin, cafeic acid, rosmarinic acid, kamferol, camphene, limonene, piperin, piplartin, santalol, sesquiterpenes, timolol, carvacrol, hidroquinone, apigenol.

For example, plant extracts with analgesic properties include extracts from the following plants: *Allium cepa, Avena sativa, Brassica nigra, Brassica oleracea, Daphne mezereum, Geranium robertianum, Geum* spp. (rivale, urbanum), *Hedera helix, Helleborus purpuranscens, Hordeum vulgare, Hyoscyami folium, Hypericum perforatum, Hypericum perforatum, Juniperus communis, Levisticum officinale, Matricaria recutita, Melissa officinalis, Mentha spicata, Petroselinum crispum, Pinus* spp., *Primula* spp. (veris, officinalis), *Pulsatilla montana, Ranunculus acris, Robinia pseudacacia, Ruta graveolens, Salix alba, Sambuccus nigra, Solanum nigrum, Solidago virgaurea, Spiraeaulmaria, Symphytum officinale, Trifolium pratense, Triticum vulgare, Veronica officinalis.*

Optionally, plant extracts with known antimicrobial properties include extracts from the following plants: *Abies alba, Abies balsamea, Abrus precatorius, Acacia dealbata, Acacia farnesiana, Achilea millefolium, Adhatoda zeilanica* (vasica), *Allium cepa, Ammonum aromaticum, Amyris balsamifera, Anthemis nobilis, Anthriscus cerefolium, Artemisia dracunculus, Artemisia princeps, Arum maculatum, Apium graveolens, Arctostaphylus uva ursi, Armeria maritime, Artemisia capillaris, Artemisia absinthium, Baptisia tinctoria, Barosma betulina, Berberis aristata, Betonica officinalis, Betula alba, Boswellia carterii, Brassica alba, Brassica rapa, Carum carvi, Carum petroselinum, Calendula officinalis, Calluna vulgaris, Cananga odorata, Capsella bursae pastoris, Carthamus tinctorius, Cedrus atlantica, Chelidonium majus, Citrus aurantifolia, Citrus aurantium, Citrus limonum, Citrus paradisi, Citrus reticulata, Cnicus benedictus, Commiphora mukul, Commiphore wightii, Copaifera officinalis, Cupressus sempervirens, Curcuma longa, Cymbopogon flexuosus, Cymbopogon martinu, Cybopogon nardus, Daucus carota, Elettaria cardamomum, Eryngium planum, Eucalyptus* spp., *Eugenia caryophyllus, Euphrasia officinalis, Evernia prunastri, Fagus sylvatica, Ferula assa foetida, Foeniculum vulgare, Gardenia florida, Gaultheria fragrantissima, Gentiana lutea, Geranium maculatum, Geum urbanum, Guajacum officinale, Hyacinthus orientalis, Hyssopus officinalis, Illicium verum, Inula helenium, Jasminum officinale, Juniperus communis, Juniperus virginiana, Laurus nobilis, Lawsonia inermis, Lippia citriodora, Litseacubeba, Marrubium vulgare, Matricaria chamomilla, Melissa officinalis, Melaleuca alternifolia, Melaleuca cajeputii, Myristica officinalis, Nymphaea odorata, Origanum vulgare, Ocimum basilicum, Olea europaea, Onopordon acanthium, Piper longum, Pelargonium* spp., *Picea excelsa, Pimenta* spp., *Pimpinella anisum, Pinus* spp., *Polygonum bistorta, Populus* spp., *Prunus amygdalus, Pseudotsuga menziesii, Pulmonaria officinalis, Pyrus malus, Quercus* spp. (alba, petraea, robur, etc.), *Quillaja* spp., *Rehmannia chinensis, Robinia pseudacacia, Rosmarinus officinalis, Rubia cordifolia, Ruta graveolens, Saccharum officinarum, Salix* spp., *Salvia officinalis, Salvia sclarea, Sambuccus nigra, Sanguisorba officinalis, Santalum album, Sassafras officinale, Solanum nigrum, Solidago virgaurea, Stephania tetrandra, Styrax benzoin, Swertia chirayta, Tamarindus indica, Thymus* spp. (vulgaris, etc.), *Trigonella foenum graecum, Turnera diffusa, Vaccinium* spp. (myrtillus, vitis idaea, etc.), *Vetiveria zizanoides, Viola odorata, Zingiber officinale, Zizyphys spina Cristi.*

In some embodiments of the present invention, the extracts with antirheumatic properties include extracts of plants, which include one or more of the following substances in vivo: saponosides, flavonoids, quercetin, luteol, salicin, taraxerol, other triterpenoids.

For example, extracts with anti-rheumatic properties include extracts from the following plants: *Abies alba, Acorns calamus, Aesculus hippocastanum, Agrimonia eupatoria, Alliaria petiolata, Allium cepa, Allium sativum, Alnus glutinosa, Anchusa officinalis, Apium graveolens, Arctium lappa, Arctostaphylos uva-ursi, Armoracia lapathifolia. Arnica Montana, Artemisia abrotanum, Artemisia dracunculus, Artemisia vulgaris, Ballota nigra, Berberis vulgaris, Betula pendula, Brassica negra, Brassica oleracea, Brassica oleracea, Brassica oleracea sabauda, Brassica pekinensis, Bryonia alba, Buxus sempervirens, Calluna vulgaris, Carthamus tinctorius, Cerasus vulgaris, Cichorium intybus, Cucumis melo, Cucurbita pepo giromontia, Dryopteris filixmas, Equisetum arvense, Erigeron Canadensis, Euonymus europaea, Eupatorium cannabinum, Fagus sylvatica, Filipendula ulmaria, Fragaria moschata, Fragaria vesca, Frasinus excelsior, Galium verum, Genista tinctoria, Glycine max, Hedera helix, Helichrysum arenarium, Hippophae rhamnoides, Hordeum distichon, Hordeum vulgare, Hyoscyamus niger, Hyssopus officinalis, Inula helenium, Juglans regia, Juniperus communis, Lamiun purpureum, Laurus nobilis, Leonorus cardiaca, Ligustrum vulgare, Lycopersicon esculentum, Lysimachia nummularia, Malus domestica, Matricaria recutita, Melilotus officinalis, Mentha piperita, Mentha spicata, Mespilus germanica, Olea europaea, Ononis spinosa, Padus avium, Paeonia officinalis, Persica vulgaris, Petasites hybridus, Petroselinum crispum, Phaseolus vulgaris, Physalis alkekengi, Picea abies, Pinus mugo, Polygala amara, Polygonum aviculare, Pulsatilla Montana, Pyrus communis, Ranunculus acris, Raphanus sativus niger, Raphanus sativus sativus, Ribes nigrum, Ribes uvacrispa, Rubus idaeus, Salix alba, Salvia glutinosa, Salvia sclarea, Sambuccus nigra, Sambucus ebulus, Scopolia carniolica, Scrophularia nodosa, Solanum dulcamara, Solanum tuberosum, Sorbus aucuparia, Spinacea oleracea, Symphytum officinalis, Syringa vulgaris, Tamarix ramosissima, Tamus communis, Taraxacum officinale, Teucrium chamaedrys, Urtica dioica, Urtica urens, Vaccinium myrtillus, Vaccinium vitis-idaea, Verbena officinalis, Veronica officinalis, Vicia faba, Vitis vinifera.*

The fatty plant extracts are composed primarily of fatty acids, both unsaturated and saturated, which decrease the production of pro-inflammatory molecules locally (eicosanoides, arachidonic acid) and inhibit the production of cytokines and chemoattractants for the cellular effectors of inflammation (macrofages, lymphocytes, etc.). All these plants have in their composition various amounts of glycerin esters of unsaturated fatty acids oleate (monounsaturated), linoleate (polyunsaturated), and alpha-linolenate (polyunsaturated), etc. and furthermore other ingredients of shea butter (triterpenes cinnamates and acetates) were shown to exert direct anti-inflammatory actions.

Some plant extracts act in a synergistic fashion towards improving the structure and function of the cartilage and ligaments which form the joints by exerting stimulatory or inhibitory effects on molecules belonging to related biological systems and therefore have a multitude of known activities including: anti-inflammatory, stimulation of formation of collagen, antiseptic properties, antioxidant, neutralizing free radicals, antiedematous, vitaminizing, and some stimulate wound healing.

The fatty extract used as base for the mixture can be any fatty plant extract. It can be a single type, or a combination of. The following are successfully examples: palm oil, palm kernel oil, coconut oil, cocoa butter, shea butter, beeswax, soy wax. They can be used interchangeably. Fatty acids with more stearic acid esters (which are solid at room temperature), help to create a more solid base. Oily extracts of any plant can be used as a base for the mixture. If the fatty acid used is fluid at room temperature this helps form a more fluid base that can be dispensed from a vial with a pump. Hydrogenated plant fats can be used (soy wax is an example) but they do have some pro-inflammatory actions that may be inversely affecting the health of the joints and surrounding tissues.

The composition of the present invention can be applied on the skin as a cream, ointment, balm, solid bar, or fluid (emulsion) from a vial either by manually squeezing the vial or by a pumping mechanism. The composition of the present invention may be further used for treating the following conditions: rheumatic disease of the joints; osteoarthritis, pain and/or swelling of joints associated with degenerative disease (rheumatoid arthritis, arthritis from various etiologies) or post-traumatic, lumbago, cervical spondylosis, lumbar pain, lombo-sciatic pain, gonarthrosis, ankle swelling and pain. The composition of the present invention may also encourage rapid recovery of various joints after strains and sprains, and reduce damage after ligament and/or cartilage tear. Thus, the composition of the present invention alleviates joint pain and swelling, and therefore increases mobility (range of motion) of rheumatic joints. Moreover, the composition alleviates swelling (edema) after a joint trauma (strain or sprain) and greatly increases the rapidity of recovery after such a trauma. Post-surgical swelling of the joints or periosteum (part of the bone)—bone edema—has also been successfully treated with this composition, making it useful in rapid post-surgical recovery.

Another aspect of some embodiments of the present invention relates to a method for extraction of the active ingredients from plants. This extraction method is optionally used for preparing the composition described above. The method of the present invention is novel and superior to previous methods of extraction, because it is performed without heating the plants. In this manner, a higher proportion of the plant's natural enzymes and ingredients is preserved.

The method of the present invention includes the following steps.

Step 1: The plants chosen for the composition are selected and each plant is milled or triturated in fresh or dried condition. The powder or paste thus obtained is mixed with dimethyl sulfoxide in a ration between from 1:1 (powder/paste: DMSO) to 1:5 by mass. In some embodiments of the present invention, the quantity of DMSO mixed with powder/paste extracted from dry plants is greater than the quantity of DMSO mixed with powder/paste extracted from fresh plants.

Step 2: The resulting mixture is pressed and sifted and the resulting liquid mixture is collected.

Step 3: The vegetal fat and the liquid mix obtained from step 2 are mixed together and additional plant oils, powder, paste and/or allantoin are added and mixed until the desired consistency is obtained.

Allantoin and/or potassium alum may be added to the mix in any one, some, or all of the above steps.

Some plants are used whole while for some just specific parts are used; likewise some plants are used in dried form while others are used fresh.

The composition of the present invention, in a non-limiting example, is in the form of an ointment. The ointment is configured for being applied to clean skin in areas of the skin adjacent to the involved joint and is rubbed into the skin with a gentle massaging action. A user may select the amount to use, but a typical use may be about 3-5 grams.

In further non-limiting examples the form may differ. The form of the composition in other embodiments may be solid and used as a bar. It may also be fluid such as a cream, emulsion, or gel. Changes in viscosity may relate to which fatty extracts are used and which form a user prefers. These changes would enable different functional packaging including allowing the invention to either be pumped through a mechanical pumping action or being scooped out by hand.

In another variant, a method for creating a composition that improves the health status of various tissues of the human body on which it is applied, comprising the following steps. Step 1: heating a fatty plant extract, beeswax, soy wax or other natural sources of non-hydrogenated solid fats until melting, then adding and mixing together one or more plants with specific properties (analgesic, anti-rheumatic, anti-inflammatory, anti-microbial), forming a mixture; those plants can be represented as their parts (leaves, roots, etc.) or whole, fresh or dried, triturated or pulverized; Step 2: cooling and re-heating, mixing the mixture for one or a few more times the resulting mixture, thus ensuring the breaking of the vegetal cellular wall and better extraction of active ingredients forom plants; and Step 3: separating and sifting the plants from the fatty mixture. Dimethylsulfoxide, and/or allantoin, and/or potassium alum and/or other plant extracts may be added as needed While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more", "at least", "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method for creating a composition that alleviates articular pain, articular inflammation, and articular swelling, the method comprising:
    milling or triturating a fresh or dried plant selected from the group consisting of *Geranium robertianum, Pinus* spp., *Arctium lappa, Ribes nigrum*, or any mixture thereof and obtaining a powder or paste and mixing with dimethyl sulfoxide as a solvent in a ratio between the powder/paste and the dimethyl sulfoxide between from 1:1 to 1:5 by mass, to form a mixture;
    pressing and sifting the mixture and collecting a liquid mixture which comprises dimethyl sulfoxide; and
    mixing the liquid mixture and a vegetal fat selected from palm oil, shea butter, or a combination thereof and adding at least one of additional plant oils, powder, or paste and mixing until a final form of the composition is obtained, the final form being a solid bar or a fluid, the final form of the composition comprising an amount of dimethyl sulfoxide effective to enhance absorption of the composition through skin and joint capsule of a user of the composition.

2. The method of claim 1 wherein the plant that is milled or triturated is whole, in parts, or in powder form.

3. The method of claim 1, wherein Allantoin and/or potassium alum is added to the mixture in any one, some, or all of the above steps.

4. The method of claim 1, wherein the amount of dimethyl sulfoxide is effective to have anti-inflammatory and/or antioxidant properties to treat an inflamed or deteriorating joint.

* * * * *